US012383645B2

(12) United States Patent
Lepore

(10) Patent No.: US 12,383,645 B2
(45) Date of Patent: Aug. 12, 2025

(54) DISINFECTION APPARATUS AND METHOD

(71) Applicant: Lorenzo Lepore, Medford, MA (US)

(72) Inventor: Lorenzo Lepore, Medford, MA (US)

(*) Notice: Subject to any disclaimer, the term of this patent is extended or adjusted under 35 U.S.C. 154(b) by 0 days.

(21) Appl. No.: 18/204,654

(22) Filed: Jun. 1, 2023

(65) Prior Publication Data

US 2024/0173449 A1 May 30, 2024

Related U.S. Application Data

(63) Continuation-in-part of application No. 17/505,538, filed on Oct. 19, 2021, now abandoned, which is a continuation-in-part of application No. 17/392,001, filed on Aug. 2, 2021.

(60) Provisional application No. 63/184,416, filed on May 5, 2021, provisional application No. 63/061,055, filed on Aug. 4, 2020.

(51) Int. Cl.
*A61L 2/22* (2006.01)
*A01N 31/02* (2006.01)
*A01N 43/16* (2006.01)
*A01N 59/00* (2006.01)
*A61L 2/26* (2006.01)
*A61L 101/02* (2006.01)
*A61L 101/34* (2006.01)

(52) U.S. Cl.
CPC ............... *A61L 2/22* (2013.01); *A01N 31/02* (2013.01); *A01N 43/16* (2013.01); *A01N 59/00* (2013.01); *A61L 2/26* (2013.01); *A61L 2101/02* (2020.08); *A61L 2101/34* (2020.08); *A61L 2202/122* (2013.01); *A61L 2202/123* (2013.01)

(58) Field of Classification Search
CPC .......... A61L 2/22; A61L 2/26; A61L 2101/02; A61L 2101/34; A61L 2202/122; A61L 2202/123; A01N 31/02; A01N 43/16; A01N 59/00
See application file for complete search history.

(56) References Cited

U.S. PATENT DOCUMENTS

2003/0170142 A1* 9/2003 Lepore .................... A61L 2/206
422/33
2005/0042130 A1* 2/2005 Lin ......................... A61L 2/208
422/33
(Continued)

FOREIGN PATENT DOCUMENTS

AT 518969 A1 * 2/2018
CN 107978305 A * 5/2018 ............... G10G 5/00
(Continued)

OTHER PUBLICATIONS

Allcases, Rekkstin & Associates, Inc., webpage titled "Mobile Master 8" (Year: 2025).*

*Primary Examiner* — Jennifer Wecker
*Assistant Examiner* — Brady C Pilsbury
(74) *Attorney, Agent, or Firm* — Danielson Legal LLC

(57) ABSTRACT

Disinfecting apparatus and method. The apparatus may include an enclosure configured to receive a device to be at least partially disinfected; an inlet port operably positioned with respect to the enclosure and configured to receive a disinfectant agent from a source and guide the disinfectant agent to at least partially disinfect the device, and an outlet port including a filter portion to at least minimize an amount of disinfectant agent that exits the enclosure.

12 Claims, 9 Drawing Sheets

(56) References Cited

U.S. PATENT DOCUMENTS

| | | | | |
|---|---|---|---|---|
| 2008/0267819 A1* | 10/2008 | Bacik | ................... | A61L 2/208 |
| | | | | 422/291 |
| 2011/0135537 A1* | 6/2011 | Schwartz | ................ | A61L 2/26 |
| | | | | 422/292 |
| 2017/0266331 A1* | 9/2017 | Liu | ........................ | A61L 2/26 |
| 2019/0314535 A1* | 10/2019 | Golkowski | ............ | A61L 2/208 |
| 2020/0230662 A1* | 7/2020 | Acquadro | ............... | G10G 5/00 |

FOREIGN PATENT DOCUMENTS

| | | | | |
|---|---|---|---|---|
| CN | 209550145 U | * | 10/2019 | |
| DE | 202014101978 U1 | * | 12/2014 | ............ G10D 9/00 |
| KR | 101654168 B1 | * | 9/2016 | ............ G10D 9/06 |
| WO | WO-9725106 A1 | * | 7/1997 | ............ A01N 25/30 |

\* cited by examiner

DISINFECTION APPARATUS AND METHOD

CROSS REFERENCE TO RELATED APPLICATIONS

The present application is a continuation-in-part of U.S. patent application Ser. No. 17/505,538, filed on Oct. 19, 2021, which is a continuation-in-part of U.S. patent application Ser. No. 17/392,001, filed on Aug. 2, 2021, which claims the benefit of and priority to U.S. provisional application No. 63/061,055, filed on Aug. 4, 2020, and U.S. provisional application No. 63/184,416, filed on May 5, 2021, the entire disclosures of each of which are incorporated by reference as if set forth in their entirety herein.

TECHNICAL FIELD

Embodiments described herein generally relate to disinfectant devices and methods and, more particularly but not exclusively, to devices and methods for disinfecting surfaces.

BACKGROUND

Musical instruments provide excellent environments for the growth of infectious microbes. Their design and intended use requires users to disperse oral and pulmonary fluids within the internal tubing or casing of instrument bodies. These fluids can remain in the instrument and serve as a culture for growing infectious microbes.

The recent COVID-19 pandemic has generated a heightened concern for microbial disease transmission. Disease transmission may occur through mucous membranes in the eyes, nose, or mouth. Wind instruments, for example, directly contact the mucous membranes of a user's mouth and come into close proximity with highly vulnerable pulmonary tissues. However, other contaminated instruments that only touch a user's skin still pose the risk of disease spread.

This is problematic in facilities such as schools, where multiple students use or handle the same instrument. Similarly, businesses such as music shops or pawn shops may only wipe external surfaces of instrument mouthpieces between different people using the instrument. As these instruments are not adequately disinfected, they can be a safety hazard to anyone who plays or handles the instrument.

Online marketplaces and ecommerce services also enable parties to exchange instruments, among other goods. These services allow people or organizations to exchange goods from essentially anywhere, including from foreign countries. These services also provide no safeguards or guarantees that a seller will take adequate safety measures before shipping an instrument to a buyer.

Also, other areas such as transportation vehicles (e.g., trains, busses, and aircraft) carry a large number of people and in a relatively small space. Passengers and crew contact several surfaces in these vehicles, and consequently these surfaces can be depository for microbes.

A need exists, therefore, for devices and methods for disinfecting instruments.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

According to one aspect, embodiments relate to a disinfecting apparatus. The apparatus includes an enclosure configured to receive a device to be at least partially disinfected; an inlet port operably positioned with respect to the enclosure and configured to receive a disinfectant agent from a source, and guide the disinfectant agent to at least partially disinfect the device; and an outlet port including a filter portion to at least minimize an amount of disinfectant agent that exits the enclosure.

In some embodiments, the device to be at least partially disinfected is a musical instrument. In some embodiments, the disinfecting apparatus further includes an adaptor extending from the inlet port and configured to be operably connected with the musical instrument to at least partially disinfect the musical instrument.

In some embodiments, the adaptor portion is insertable into a lumen of the musical instrument.

In some embodiments, the disinfectant agent comprising 6-8% hydrogen peroxide. In some embodiments, the disinfectant agent further comprises isopropyl alcohol. In some embodiments, the disinfectant agent further comprises eucalyptol oil In some embodiments, the disinfectant agent is introduced into the device as a mist.

In some embodiments, the enclosure includes a removable top portion that is hermetically sealable with the enclosure.

According to another aspect, embodiments relate to a disinfectant agent for at least partially disinfecting a device, the disinfectant agent comprising 6-8% hydrogen peroxide. In some embodiments, the disinfectant agent further comprises isopropyl alcohol. In some embodiments, the disinfectant agent further comprises eucalyptol oil.

In some embodiments, the device is a musical instrument.

According to yet another aspect, embodiments relate to a method for at least partially disinfecting an instrument. The method includes operably positioning an instrument with respect to the enclosure of the disinfecting apparatus described above; connecting the inlet port to the source of the disinfect agent; and enabling the disinfectant agent to travel from the source to the instrument to at least partially disinfect the instrument.

In some embodiments, the disinfectant agent comprising 6-8% hydrogen peroxide. In some embodiments, the disinfectant agent further comprises isopropyl alcohol. In some embodiments, the disinfectant agent further comprises eucalyptol oil.

In some embodiments, the disinfectant agent is introduced into the instrument as a mist.

In some embodiments, the method further includes adjusting a rate at which the disinfectant agent travels from the source to the instrument.

BRIEF DESCRIPTION OF DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1:
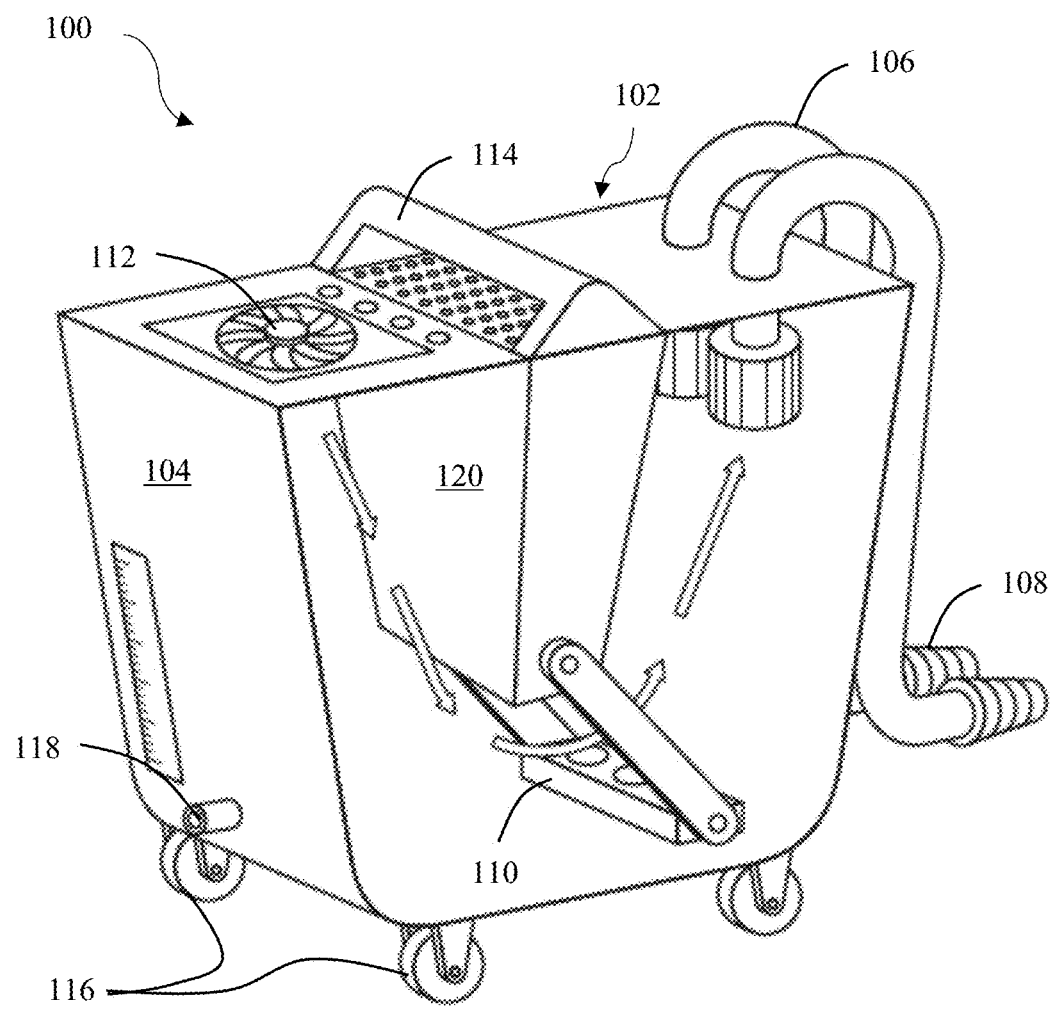
FIG. 1 illustrates a disinfecting apparatus in accordance with one embodiment.

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

As discussed above, musical instruments provide excellent environments for the growth of infectious microbes. In schools, for example, multiple students may use the same instrument as part of their music classes, and these instruments are rarely disinfected between uses. For example, a school's disinfectant procedure may involve only wiping the mouthpieces of instruments between uses. Schools may occasionally send instruments out for a more thorough cleaning or disinfection procedure, but this tends to occur infrequently and still does not adequately disinfect the instruments.

There is also no way to ensure the health of all instrument users. Accordingly, students may be at risk of passing along and being exposed to harmful microbes from other, possibly ill students.

Numerous peer reviewed and published medical studies have demonstrated that wind instruments in particular enable the growth of infectious microbes because of their internal tubing. These instruments also directly contact the mucous membranes of a user's mouth, which are in close proximity to highly vulnerable pulmonary tissues. However, even other instruments that only touch a user's skin still pose a health risk to users.

Instruments are often stored in instrument cases for an extended period of time as well. Students may go several days without removing their instrument from the instrument's case. The dark, moist environment of the case's interior is also conducive to microbe growth.

Embodiments described herein provide devices and methods for disinfecting instruments or other devices or surfaces. The term "disinfect" as used in the present application may refer to the process of removing microbes or microorganisms such as bacterium or viruses (for simplicity, "microbes"). In the context of the present application, "microbes" may also refer to substances that could cause disease or otherwise bring harm to a person if the person were exposed to said substances.

The term "disinfect" recognizes that not all microbes may be removed by the embodiments herein. For example, some instruments such as French horns have up to 18 feet of tubing and a disinfectant agent may not "reach" all internal surfaces thereof in casual use. Accordingly, the disinfectant agent described below may not contact every surface of an instrument to remove all microbes from the instrument but will still greatly minimize the risk of microbial transmission.

Even if the disinfectant agent reaches a particular surface, the agent may not remove 100% of the microbes from the surface. Accordingly, "disinfect" may refer to the process of removing at least some amount of microbes such that a person is less likely to be exposed to microbes had the disinfectant process not been performed.

The embodiments of the present application provide devices and methods for disinfecting a musical instrument. FIG. 1 illustrates a disinfecting apparatus 100 in accordance with one embodiment. The apparatus 100 may include a disinfectant generator 102 with a tank 104, one or more hoses 106, and one or more nozzles or adaptors 108.

The disinfectant generator 102 may include one or more ultrasonic transducers 110 in the tank 104 to convert a liquid (not shown in FIG. 1) to a mist or fog to act as a disinfectant agent. The disinfectant generator 102 may include a pressure fan 112 to force the disinfectant agent through the hose(s) 106 and into an instrument (also not shown in FIG. 1).

The disinfectant generator 102 may further include, for example, a handle 114 to facilitate carrying of the disinfectant generator 102, wheels 116 to facilitate movement of the generator 102, and a drain 118 to remove liquid from the tank 104. The disinfectant generator 102 may also include any required electronics 120 to power the apparatus 100 and control the operation of components thereof.

Figure 2:
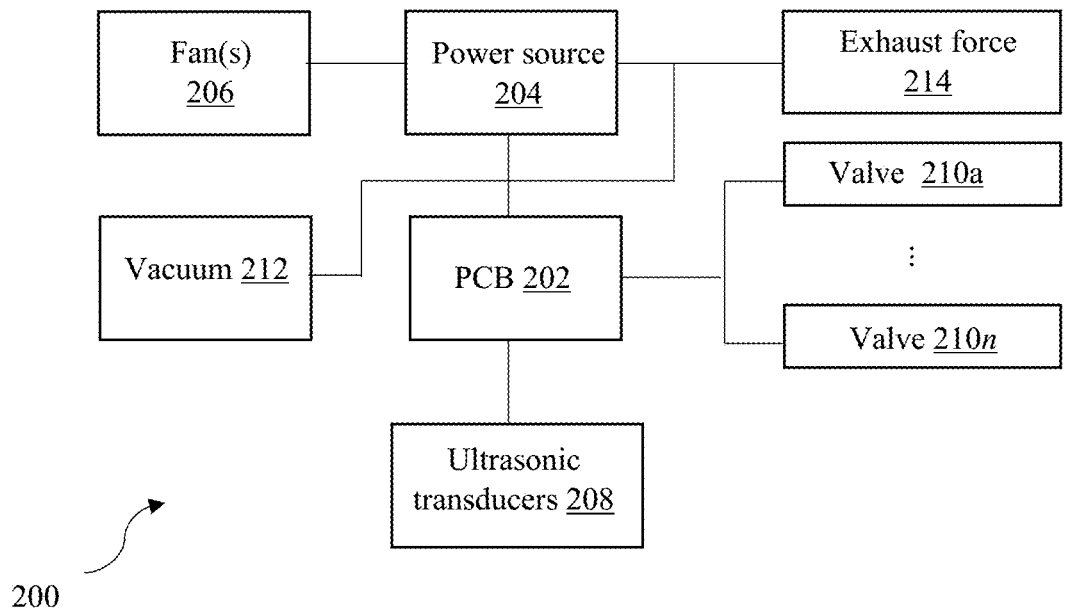
FIG. 2 illustrates a diagram of the electronics of the disinfecting apparatus of FIG. 1 in accordance with one embodiment.

FIG. 2 illustrates an electrical diagram 200 of the electronics 120 of FIG. 1. The electronics 120 may include a printed circuit board (for simplicity, "PCB") 202 in connection with a power source 204. The PCB 202 may be in operable communication with and issue instructions to one or more fan controllers 206, ultrasonic transducer(s) 208, and valves 210a-n where n is the number of valves configured with the disinfectant generator. For example, there may a valve associated with each hose extending from the disinfectant generator. The PCB 202 may instruct a particular valve 210 to open to allow the disinfectant agent to flow through its associated hose, or to close to prevent the disinfectant agent from flowing through its associated hose.

The PCB 202 and power source 204 may instruct and supply power to the ultrasonic transducer(s) 208. For example, upon activation, the ultrasonic transducer(s) 208 may vibrate or create waves to volatilize the liquid agent in the disinfectant generator into the disinfectant agent.

Some embodiments of the disinfectant generator may use an ionized hydrogen peroxide process to disinfect an instrument. For example, some embodiments may apply Binary Ionization Technology™ to a low-percentage Hydrogen Peroxide ($H_2O_2$)-based solution to create an activated ionized hydrogen peroxide (for simplicity, "AIHP") fog or mist that is applied to surfaces of an instrument to disinfect the instrument. After exposure to cold plasma activation, the hydrogen peroxide is converted to OH ions such as hydroxyl radicals, which are a type of reactive oxygen species. This reactive oxygen species damages pathogenic organisms through oxidation of proteins, carbohydrates, and lipids. This damage leads to cellular disruptions or dysfunctions, thereby disinfecting targeted surfaces.

Accordingly, hydrogen peroxide is a liquid disinfectant that can be used as an active ingredient in the disclosed embodiments. The described embodiments may atomize the solution into a gaseous mist that at least partially disinfects a device such as a musical instrument. Hydrogen peroxide is a low-temperature disinfectant, which makes it a good option for use with heat-sensitive materials, such as those commonly used in medical devices and musical instruments. Due to material compatibility issues and the vast array of diverse components of devices such as musical wind instruments, the disclosed embodiments not only disinfect, but do so without damaging the instruments.

The disinfectant agent described herein may include various amounts of hydrogen peroxide. For example, in some embodiments, the solution may comprise 6-8% hydrogen peroxide. These levels may be low enough to comply with any mandates or environmental regulations, while high enough to at least partially disinfect a device.

In some embodiments, the disinfectant agent may further include one or more additives. For example, the disinfectant agent may include small amounts of eucalyptol oil. In some embodiments, the disinfectant agent may include isopropyl alcohol. While these additives are anti-microbial, they may also provide a pleasant aroma to the disinfectant agent or otherwise to the disinfectant process.

The exact proportions of the various additives, compounds, or substances of the disinfectant agent may vary. The volume(s) may depend on the physical constraints of the disinfectant generator as well. For example, for every two gallons of hydrogen peroxide, there may be two drops of eucalyptol oil and two drops of isopropyl alcohol.

The descried chemical formulations and associated processes are only exemplary and do not limit the disinfectant agent to a particular substance or process. Other types of disinfectant agents may be used as long as they can disinfect surfaces to accomplish the objectives of the embodiments described herein.

The PCB 202 may also control the amount of power supplied from the power source 204 to the various components of the disinfectant generator. For example, if multiple valves are open, the fan(s) may require more power to adequately emit the disinfectant agent through multiple hoses. If the disinfectant generator has only one valve (or only one valve that is open), the power source 204 may supply less power to the fans to adequately emit the disinfectant agent through the hose and conserve power.

Similarly, different instruments may require different pressure drives. This may be due to the size of the instrument or the anatomy of the instrument. For example, a straight tube instrument such as a clarinet or a flute may require a less intense pressure drive than that of a French horn or other type of instrument with narrow and convoluted pathways from the mouthpiece to the bell.

With multiple hoses, the disinfectant generator may accommodate multiple instruments or surfaces per disinfectant application or cycle. In some embodiments, the disinfection capacity would be limited only by the size of the tank that holds the liquid disinfectant.

In some embodiments, multiple hoses with adaptors may service different parts of a single instrument. For example, a hose with one adaptor may disinfect the bell of an instrument while another hose with a different adaptor may simultaneously disinfect the mouthpiece of the instrument.

In some embodiments, the disinfectant generator may further include a vacuum device 212 for removing moisture remaining from the disinfectant process. For example, the vacuum device 212 may comprise an output adaptor that is shaped and sized to fit in the bell of an instrument to create a seal therewith. During a vacuum operation, a vacuum device 212 such as a Venturi vacuum generator cartridge may draw in air through an output adaptor and, as a result, remove any moisture from the instrument. In some embodiments, the output adaptor may comprise an indicator to validate that the disinfectant agent has passed through the instrument or that the instrument interior is dry.

In some embodiments, the PCB 202 and the power source 204 may also be in operable connectivity with an exhaust force generator 214. The exhaust force generator 214 may generate an exhaust force through the instrument to remove moisture from the instrument. For example, the disinfectant generator may include any required blowers, pumps, tubing, or adaptors to force pressurized air through the instrument.

Referring back to FIG. 1, in operation the hose 106 may be operably positioned with respect to an instrument, such as inserted into a portion of the instrument. The disinfectant agent generated by the disinfectant generator 102 may be forced out of the tank 104, through the hose 106, and into the instrument to disinfect the instrument. For example, the hose 106 may be inserted into the bell of an instrument. To achieve a desired fit with respect to the instrument, a nozzle 108 that conforms to the shape of the instrument body (e.g., the inner surface of an instrument's bell) may be inserted into the instrument.

Figure 3:
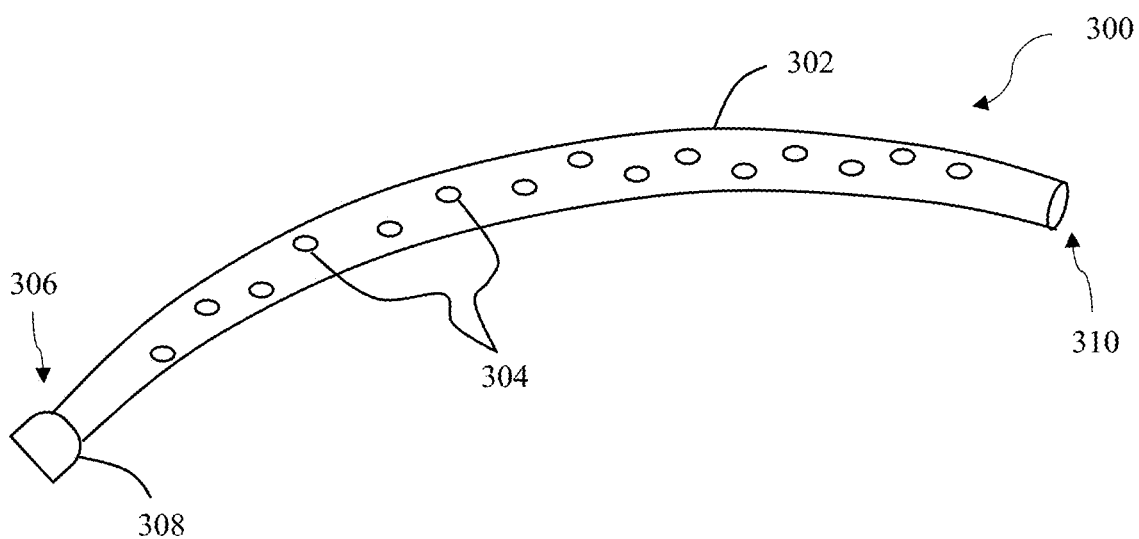
FIG. 3 illustrates a hose of the disinfecting apparatus of FIG. 1 in accordance with one embodiment.

FIG. 3 illustrates a hose 300 in accordance with one embodiment. The hose 300 may be used in conjunction with the disinfectant generator 102 of FIG. 1. The hose 300 may include a tube portion 302 with one or more apertures 304 such as holes or slits that allow a disinfectant agent to be emitted from the tube portion 302.

In operation, the proximal end 306 may be operably connected to a disinfectant generator such as the disinfectant generator 102 of FIG. 1 via a connection mechanism 308. The distal end 310 may be inserted into various locations of an instrument body or otherwise operably positioned with respect to an instrument. Upon activation, the disinfectant generator may deliver the disinfectant agent to the hose 300 such that the disinfectant agent travels through at least a portion of the tube portion 302 and out of the aperture(s) 304 or the distal end 310.

The tube portion 302 may comprise any type of material that can carry the disinfectant agent and is flexible enough to fit into an instrument. The tube portion 302 may have a customized length and width depending on the type of instrument it is intended to disinfect. For example, a thicker tube portion 302 may be used to disinfect a tuba than one used to disinfect a piccolo.

The one or more apertures 304 may allow the emission of the disinfectant agent during the disinfectant process. In some embodiments, the one or more apertures 304 may be evenly distributed along the length of the tube portion 302. In some embodiments, however, the tube portion 302 may not have any apertures 304.

The connection mechanism 308 may connect the tube portion 302 with the disinfectant generator. For example, the connection mechanism 308 may comprise a rubber plug that can deform and be placed into and seal a hole of the tank 104 by an interference or pressure fit. Alternatively, the connection mechanism 308 may include a series of threads or slots to engage a respective surface of the disinfectant generator 102.

In some embodiments, such as in FIG. 1, the hose 106 may further include a nozzle or adaptor (for simplicity, "nozzle") 108 that is configured to fit inside of an instrument body or otherwise engage an instrument. For example, the nozzle 108 may be placed within the lumen of an instrument body to create a seal therewith. The nozzle 108 may be customized to fit into a specific type of instrument, such as a specific type of wind instrument.

These nozzles may be readily exchangeable such that a user can remove a first nozzle 108 from the hose 106 and attach a second, differently-sized or shaped nozzle. For example, a nozzle for a flute may be smaller than a nozzle for a saxophone. Different nozzles may be used for the bell and joints of an instrument.

The nozzle 108 may operably connect with the hose 106 via a pressure or interference fit. Alternatively, the nozzle 108 may include a threaded portion to engage a threaded portion of the hose 106. The exact configuration of the nozzle(s) 108 and how they connect with the hose 106 may vary.

In some embodiments, the hose 106 may alternatively be configured with an adaptor. Rather than, for example, a nozzle being inserted into the lumen of an instrument, a nozzle may be configured to create a seal around one end of the instrument to drive the disinfectant agent through the instrument. For example and without limitation, the adaptor may be formed of a rubber material and configured to create a seal around the mouthpiece of an instrument.

In some embodiments, a user may create and use a mold of the mouthpiece so that the nozzle creates a seal around the instrument mouthpiece. In some embodiments, the mold may attach to the outside of the instrument.

The ultrasonic transducer(s) 110 may be activated to volatilize the liquid agent. The ultrasonic transducer(s) may comprise one or more metal plates that may, upon activation, vibrate at such frequencies to convert the liquid agent into a fog, mist, or otherwise to a gaseous state to act as the disinfectant agent. The disinfectant agent may look like smoke and provide a visual validation that the disinfectant agent has penetrated the instrument or a component thereof.

Figure 4:
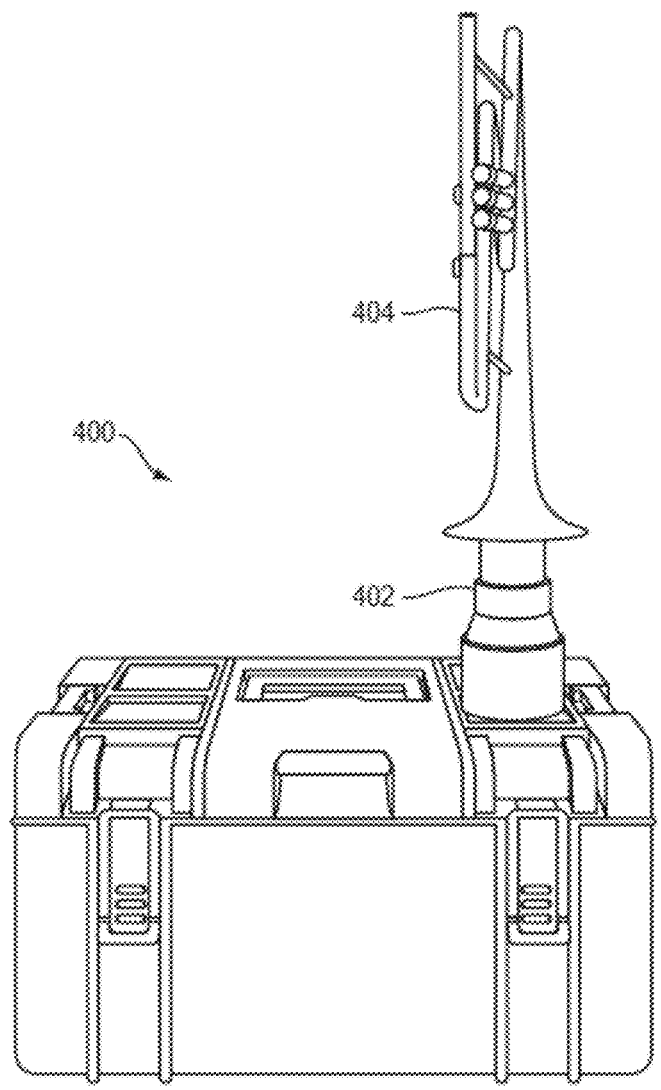
FIG. 4 illustrates a disinfecting apparatus in accordance with another embodiment.

The configuration of the instrument disinfecting apparatus 100 of FIG. 1 is merely exemplary, and the instrument disinfecting apparatus may be configured in a variety of ways. For example, FIG. 4 depicts a case 400 that may be used to transport or protect a disinfectant generator such as the disinfectant generator 102 of FIG. 1. In this embodiment, a hose may be positioned vertically and connected to a vertical adaptor or nozzle 402. In this configuration, an instrument such as a trumpet 404 may be positioned over the nozzle 402 to undergo the disinfectant process.

Figure 5:
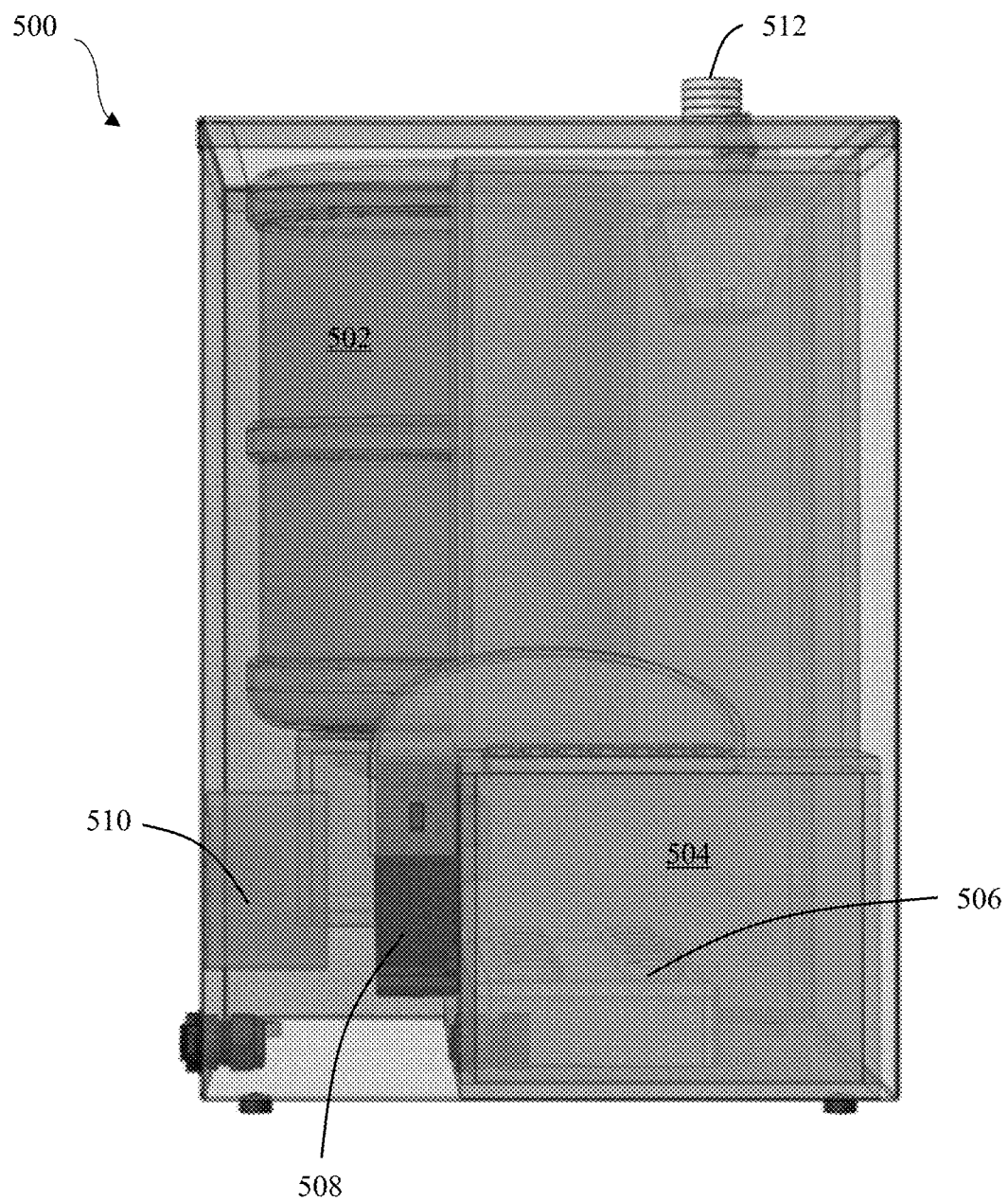
FIG. 5 illustrates a disinfecting apparatus in accordance with another embodiment.

As another example, FIG. 5 illustrates a front view of a disinfectant generator 500 in accordance with another embodiment. The disinfectant generator 500 of FIG. 5 may include a reservoir 502 to supply a liquid disinfectant to a tank 504. A mist generator 506 such as one or more ultrasonic transducers may be in operable connectivity with the tank 504 such that it can convert liquid therein to a mist. The mist generator 506 may be configured similarly to the ultrasonic transducers 110 of FIG. 1, for example.

One or more fans 508 operably positioned with respect to a fan intake 510 may force the disinfectant agent (in mist form) through the disinfectant generator 500 and out of the outlet 512. Although not shown in FIG. 5, the disinfectant generator 500 may receive at the outlet 512 a hose such as the hose 300 of FIG. 3.

Figure 6:
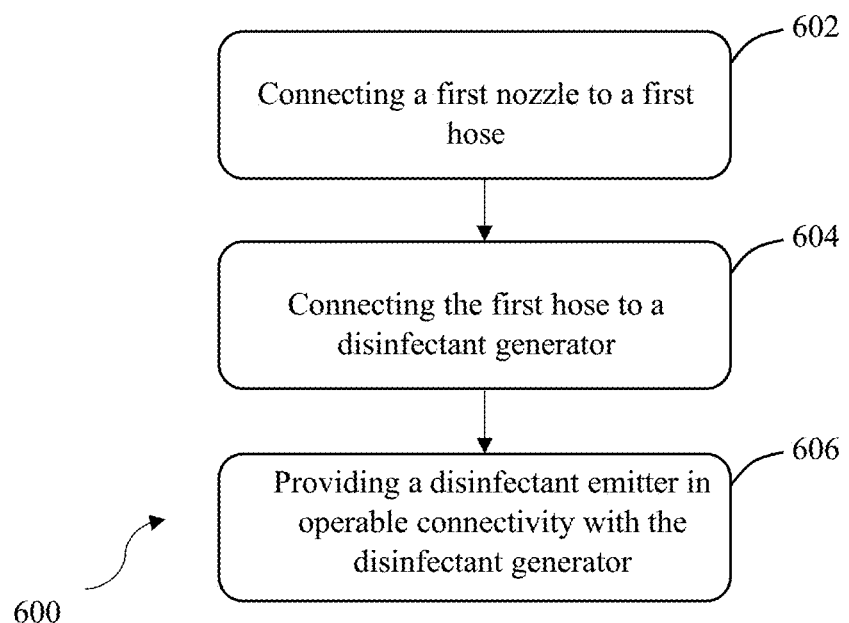
FIG. 6 depicts a flowchart of a method of manufacturing a disinfecting apparatus in accordance with one embodiment.

FIG. 6 depicts a flowchart of a method 600 for manufacturing an instrument disinfecting apparatus in accordance with one embodiment. Step 602 involves connecting a first nozzle to a first hose. The hose may be similar to the hose of FIGS. 1 and 3, for example, and may comprise a flexible tube portion that can be inserted into an instrument. Step 602 may similarly involve connecting an adaptor to the first hose in lieu of a nozzle. The nozzle or adaptor may operably connect with the first hose via a pressure or interference fit, for example.

Step 604 involves connecting the first hose to a disinfectant generator configured to hold a disinfectant agent. The disinfectant generator may be similar to the disinfectant generator 100 of FIG. 1, for example. The disinfectant generator may be configured to hold a disinfectant such as a liquid disinfectant that can be volatilized into a mist.

Step 606 involves providing a disinfectant emitter in operable connectivity with the disinfectant generator that is configured to emit the disinfectant agent through at least the first hose to disinfect an instrument. For example, the disinfectant generator may include one or more fans to help propel the disinfectant agent out of the disinfectant generator to the instrument.

Method 600 may include additional steps related to manufacturing the disinfectant generator. For example, the method may further include providing at least one ultrasonic transducer in the disinfectant generator to volatize a disinfectant liquid to a fog or mist to create the disinfectant agent, providing the disinfectant generator with a vacuum device, and creating a plurality of apertures in the first hose that are configured to emit the disinfectant agent out of the first hose to disinfect the instrument.

Although the present application is largely described in the context of disinfecting musical instruments, the embodiments described herein may be used in a variety of other applications. For example, the embodiments herein may disinfect furniture surfaces, medical equipment, sporting equipment, surfaces in transportation vehicles, tools, breathalyzers, drinkware, foodware, cookware, or the like. The above list is not exhaustive, and the embodiments described herein may disinfect other structures or devices in addition to or in lieu of those listed above.

Figure 7:
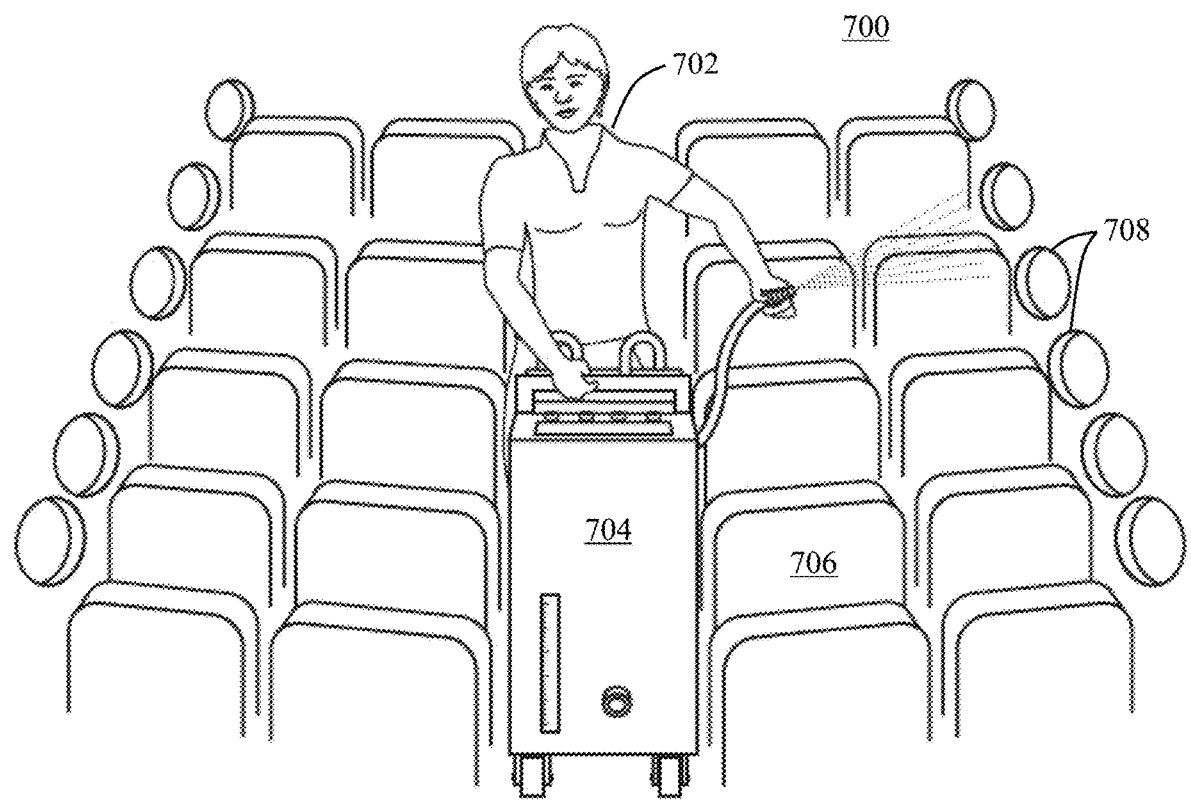
FIG. 7 illustrates user disinfecting surfaces in an airplane cabin in accordance with one embodiment.

As a more specific example of transportation vehicles, the embodiments described herein may disinfect surfaces on aircraft such as airplanes. FIG. 7 illustrates the interior of an airplane cabin 700 in which a user 702 uses a disinfecting apparatus 704 to disinfect surfaces such as those on seats 706 or windows 708. The disinfecting apparatus 704 may be similar to the disinfecting apparatus 100 of FIG. 1.

Commercial airplanes transport over one million passengers per day. Often times a single flight transports hundreds of passengers, none of whom are able to socially distance during the flight.

Although airplanes are equipped with air-filtration technologies, there is still the potential for passengers to transmit microbes onto surfaces in the airplane and to be exposed to microbes on the airplane. These surfaces may include, but are not limited to, armrests, seats, headrests, electrical outlets, tray tables, tray table locks, windows, window covers, safety pamphlets or other reading materials, fan controls, light controls, overhead storage covers, overhead storage cover handles, lavatory doors, lavatory door handles, surfaces within a lavatory, etc. Accordingly, there are plenty of surfaces to disinfect between flights.

There is typically a short window of time between when a plane is scheduled to arrive at a gate to disembark passengers, and when other passengers are scheduled to board the plane for a subsequent flight. As a result these surfaces must be disinfected as quickly as possible.

The embodiments herein may be used in conjunction with a disinfectant process to disinfect airplane surfaces. These surfaces may include those listed above, for example. In these applications, the apparatus may be held, carried, or rolled (as in FIG. 7) by a worker to emit the disinfectant on any required surfaces in the airplane. The apparatus may use any combination of tube portions, nozzles, disinfectant generators, connection mechanisms, or the like.

As another exemplary application, the embodiments described herein may disinfect surfaces in healthcare institutions such as hospitals, clinics, urgent care facilities, intensive care units, doctor's offices, or other types of locations associated with various healthcare providers. Healthcare institutions such as these treat patients, some of whom may be suffering from one or more diseases. Throughout the course of treatment, these patients and other personnel may transmit microbes onto various surfaces or objects and be exposed to microbes therefrom. This problem can be exacerbated if patients are carriers of harmful diseases.

Accordingly, healthcare institutions may face heightened pressure to disinfect various surfaces therein. These surfaces may include, but are not limited to, beds, pillows, chairs, tables, armrests, doors, door handles or knobs, nightstands, elevators, elevator buttons, kiosks, touchscreens, restrooms, trash cans, hallways, diagnostic equipment, monitoring equipment, or the like.

In these applications, the apparatus may be held, carried, or rolled by a user as the user moves through the healthcare institution and disinfects surfaces therein. The apparatus may use any combination of tube portions, nozzles, disinfectant generators, connection mechanisms, or the like.

There may be leftover or residual disinfectant agent from the disinfectant procedures described herein. For example, the disinfectant agent may enter a lumen of an instrument, travel through the instrument, and exit out of the mouth end of the instrument. However, there may be residual disinfecting agent that would be suspended in the environment external to the instrument. "Environment" may refer to the space surrounding the exterior of the instrument, such as where personnel may be operating the disinfectant apparatus.

Although hydrogen peroxide is largely harmless, it can still irritate humans. For example, hydrogen peroxide can irritate the eyes, nose, skin, mouth, and throat. Other types of disinfectant agents may be even more dangerous to humans.

It may therefore be desirable to contain any residual disinfectant agent to at least minimize the amount that could contact a person. Accordingly, in some embodiments, a containment chamber may contain the device to be at least partially disinfected during the disinfectant procedure.

Figure 8A:
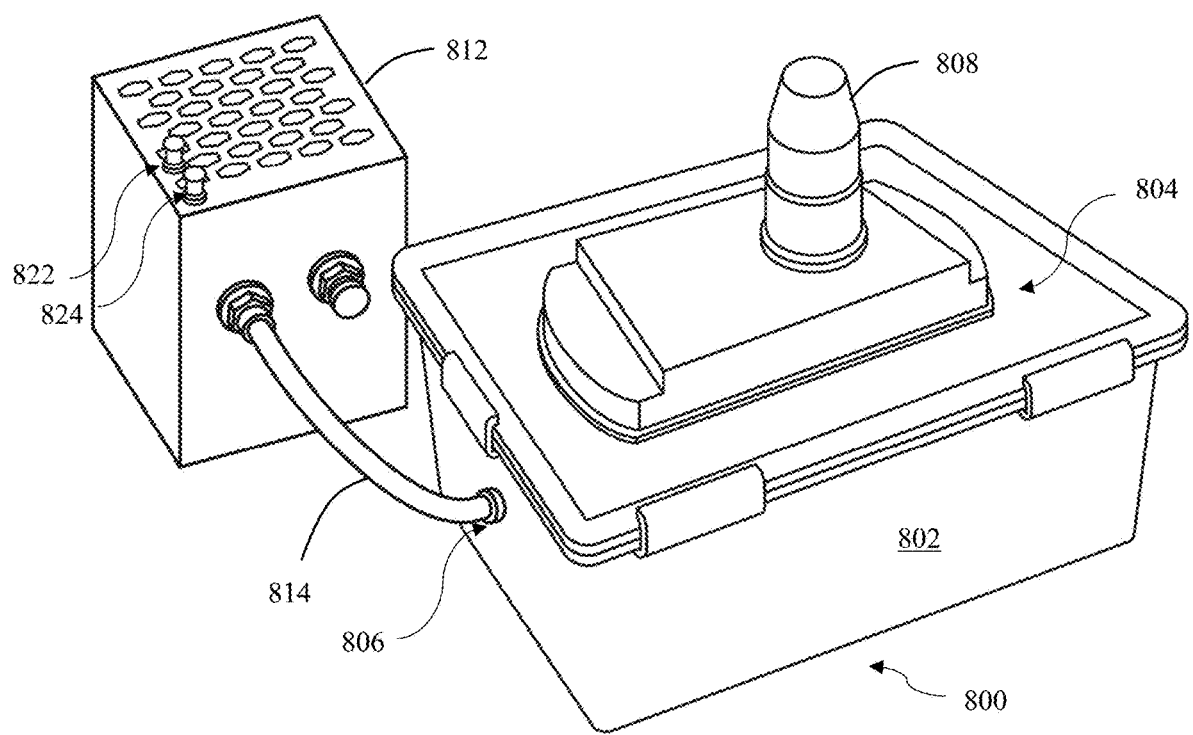
FIGS. 8A & B illustrate a containment chamber in accordance with one embodiment.
Figure 8B:
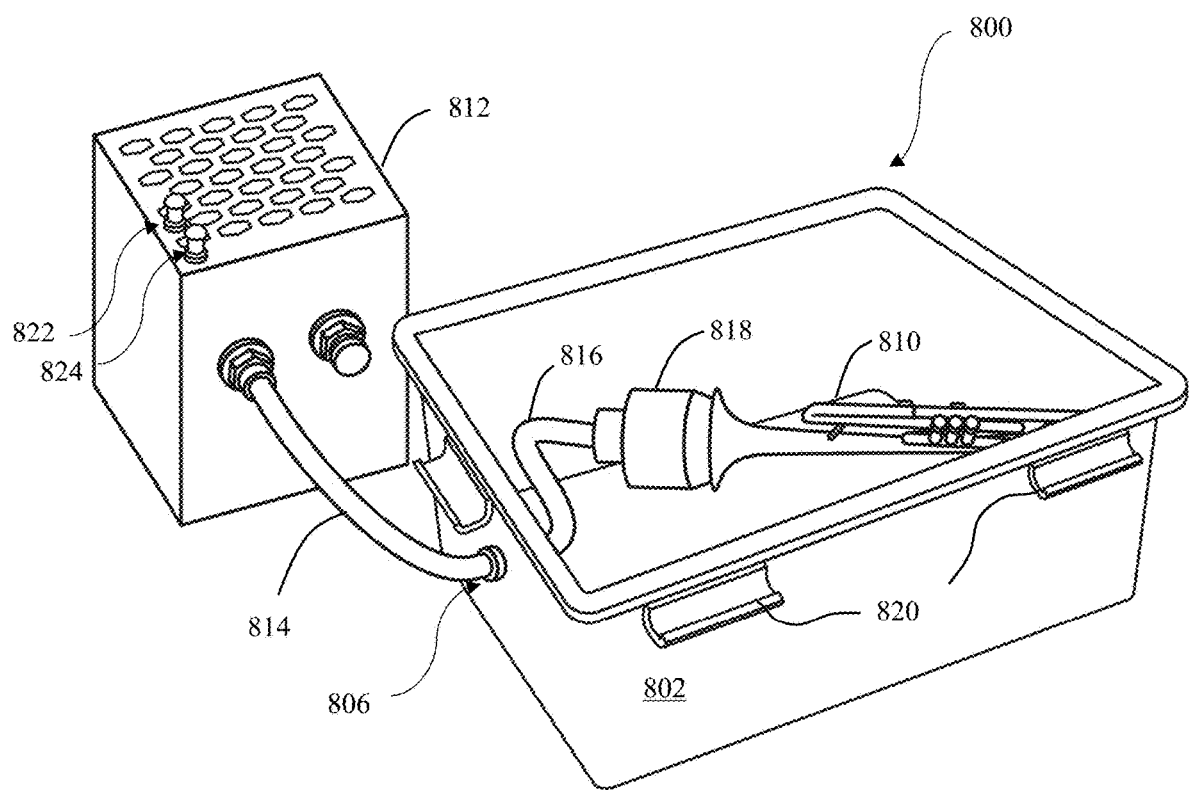

FIGS. 8A & 8B illustrate a containment chamber 800 in accordance with one embodiment. The containment chamber 800 may include a base portion 802, a top portion 804, one or more inlet ports 806, and a filter portion 808. FIG. 8A illustrates the containment chamber 800 in a closed state. FIG. 8B illustrates the containment chamber 800 in an open state.

As seen in FIG. 8B the containment chamber 800 may contain or otherwise hold a device to be at least partially disinfected, illustrated as a trumpet 810. The containment chamber 800 may be operably connected to a disinfectant apparatus 812, such as the disinfectant generator 102 of FIG. 1 or the disinfectant generator 500 of FIG. 5.

The disinfectant generator 812 can provide the containment chamber 800 with a disinfectant agent. For example, the containment chamber 800 may receive from the generator 812 a tubular portion 814 such that the disinfectant agent can be introduced into the containment chamber 800. The volatized disinfectant agent may exit the apparatus 812, travel through any connection devices or portions such as tubular portion 814, and into the containment chamber 800 via the inlet port 806 to at least partially disinfect any devices in the containment chamber 800.

In some embodiments, the inlet port 806 may include a tube portion 814 extending into the chamber. The inlet port 806 or tube portion 816 (or 814) may also include or otherwise receive one or more adaptor portions 818 that are each sized or configured to engage a certain type of device (e.g., a certain type of musical instrument). In some embodiments, the inlet port 806 may be configured with or as a mount portion, such that the device can be placed directly on the inlet port 806 to receive the disinfecting agent.

The top portion 804 may be selectively removed from and connected to the base portion 802. As seen in FIG. 8A, the top portion 804 may be secured to the base portion 802 by one or more clamps 820. The clamps 820 are merely exemplary, and other types of connection mechanisms may be used to secure the top portion 802 to the base portion 804 or otherwise to provide an enclosure. Regardless of the exact type of connection mechanisms implemented, the containment chamber 800 should be hermetically sealed to prevent undesired substances from exiting the chamber 800.

Although only one inlet port 806 and device 810 are shown in FIGS. 8A & B, the containment chamber 800 may be configured and sized to receive multiple devices. For example, the containment chamber 800 may include multiple inlet ports that are each configured to receive a disinfectant agent.

The filter portion 808 may filter any hydrogen peroxide and any other active ingredients such that they do not enter the environment. Accordingly, the filter portion 808 may prevent harmful substances (e.g., peroxide) from being inhaled by personnel or physically contacting the personnel. For example, the containment chamber may prevent any discharge of peroxide of more than 0.3 ppm, well below the OSHA-specified standard of 1.6 ppm.

The filter portion 808 may comprise any sort of configuration or material to at least reduce the amount of disinfectant particles that exit the containment chamber 800. For example, the filter portion 808 may comprise a chute portion with one or more filter elements therein. In embodiments in which the disinfectant agent is or otherwise includes hydrogen peroxide, these filter elements may include one or more carbon or catalytic carbon filtering elements to convert the mist into acceptable levels of hydrogen peroxide and, additionally, residual products of oxygen and water.

The disinfectant generator 812 in this embodiment may include a power control 822 and a mist generation control 824. The power control 822 may be in an "off" state when the disinfectant generator 812 is not in use. The disinfectant generator 812 may also include a separate fan control to control the fan speed to in turn control the volumetric flow rate of the disinfectant agent. The rate may be different for each different instrument or device to be disinfected. Additionally or alternatively, the rate may be adjusted based on the desired amount of time for a disinfectant process. For example, a lower flow rate may cause the disinfectant process take longer than a faster flow rate.

Lower flow rates may be appropriate for instruments that are generally linear in shape and do not include many turns of tubing. For example, instruments such clarinets or oboes may be sufficiently disinfected with lower flow rates. Higher flow rates may be appropriate or even necessary for instruments having greater lengths or turns of tubing to ensure the disinfectant agent can traverse the entirety of the instrument. For example, French horns or trumpets may require a higher flow rate than clarinets.

Figure 9:
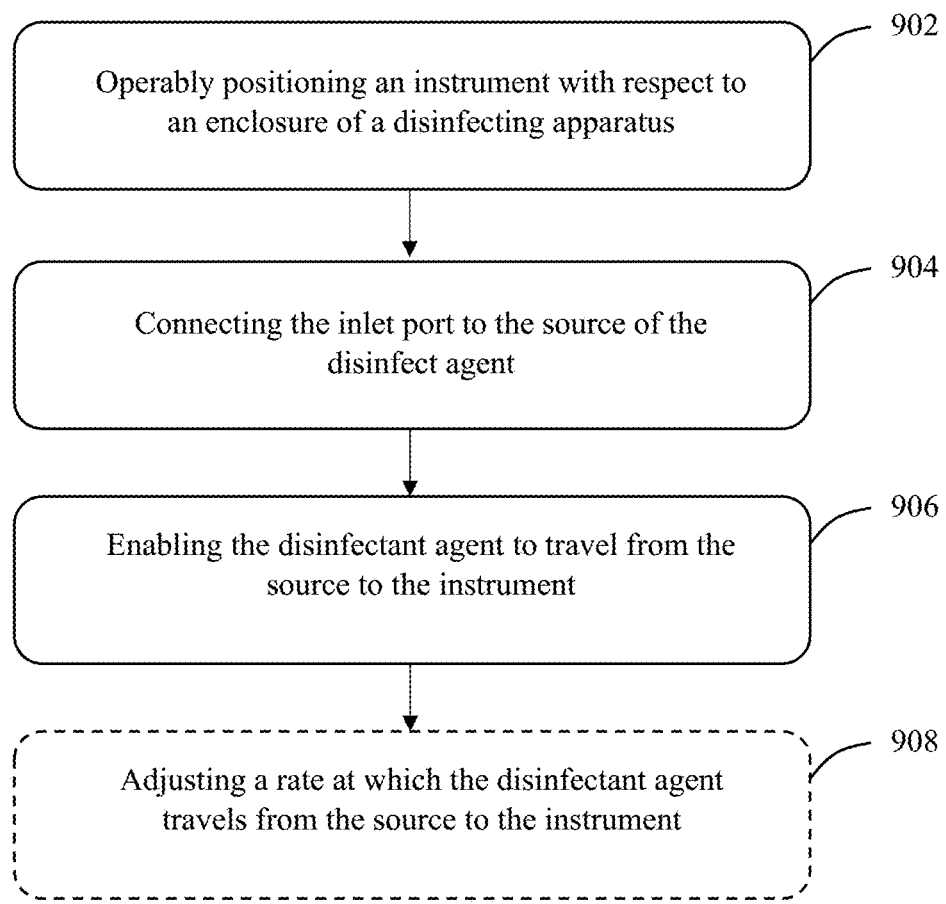
FIG. 9 depicts a flowchart of a method for at least partially disinfecting an instrument.

FIG. 9 depicts a flowchart of a method 900 for at least partially disinfecting an instrument in accordance with one embodiment. Step 902 involves operably positioning an instrument with respect to an enclosure of a disinfecting apparatus such as those described previously.

Step 902 may involve, for example, placing an instrument in the containment chamber such that it is positioned to receive a disinfectant agent from an inlet port. In some embodiments the containment chamber may include a tubular portion extending from the inlet port. In these embodiments, step 902 may involve inserting the tubular portion into the lumen of instrument.

Step 904 involves connecting the inlet port to the source of the disinfectant agent. For example, a tubular portion may fluidly connect a source such as the disinfectant apparatus described above to the containment chamber. More specifically, the tube portion may connect the to the inlet port of the containment chamber.

Step 906 involves enabling the disinfectant agent to travel from the source to the instrument to at least partially disinfect the instrument. Step 906 may involve, for example, supplying power to the disinfectant generator, activating a mist control, and activating a fan such that the generated mist (i.e., the disinfectant agent) may travel from the disinfectant generator and to the containment chamber. After a period of time, an operator may notice the disinfectant agent within the containment chamber (e.g., if the containment chamber is made of a transparent material).

Step 908 involves adjusting a rate at which the disinfectant agent travels from the source to the instrument. For example, the disinfecting apparatus such as the apparatus 500 of FIG. 5 may include a control device to adjust fan speed. This may in turn control the volumetric flow rate at which the disinfectant agent travels from the apparatus and to the containment chamber.

As discussed previously, the rate may be different for each device to be disinfected. Additionally or alternatively, the rate may be adjusted based on the desired amount of time for a disinfectant process. For example, a lower flow rate may cause the disinfectant process take longer than a faster flow rate.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, or alternatively, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims.

What is claimed is:
1. A portable disinfecting apparatus comprising:
 an enclosure configured to receive a musical instrument to be at least partially disinfected, wherein the musical instrument includes a bell and a hollow interior pathway;

an inlet port operably positioned with respect to the enclosure;

a tube portion that is configured to receive a volatized disinfectant agent from a source and further configured to extend through the inlet port and into the enclosure to guide the disinfectant agent to at least partially disinfect the musical instrument in the enclosure;

an adaptor portion configured to attach to the tube portion and further configured to contact an inner surface of the bell of the musical instrument to create a seal with the inner surface of the bell to enable the volatized disinfectant agent to travel from the source, through the adaptor, and through the hollow interior pathway of the musical instrument to at least partially disinfect the musical instrument; and an outlet port including a filter portion configured to at least minimize an amount of disinfectant agent that exits the enclosure.

2. The disinfecting apparatus of claim 1, the disinfectant agent comprising 6-8% hydrogen peroxide.

3. The disinfecting apparatus of claim 2 wherein the disinfectant agent further comprises up to 1% isopropyl alcohol.

4. The disinfecting apparatus of claim 2 wherein the disinfectant agent further comprises up to 1% eucalyptol oil.

5. The disinfecting apparatus of claim 1 wherein the disinfectant agent is introduced into the hollow interior pathway of the musical instrument as a mist.

6. The disinfecting apparatus of claim 1 wherein the enclosure includes a removable top portion that is hermetically sealable with the enclosure.

7. A method for at least partially disinfecting a musical instrument, the method comprising:

operably positioning the musical instrument with respect to the enclosure of the portable disinfecting apparatus of claim 1, wherein the musical instrument includes a bell and a hollow interior pathway;

connecting the inlet port to the source;

positioning the adaptor into an inner surface of the bell of the musical instrument to create a seal with the inner surface of the bell; and enabling the volatized disinfectant agent to travel from the source, through the adaptor, and through the hollow interior pathway of the musical instrument to at least partially disinfect the musical instrument.

8. The method of claim 7, the disinfectant agent comprising 6-8% hydrogen peroxide.

9. The method of claim 8 wherein the disinfectant agent further comprises up to 1% isopropyl alcohol.

10. The method of claim 7 wherein the disinfectant agent further comprises up to 1% eucalyptol oil.

11. The method of claim 7 wherein the disinfectant agent is introduced into the hollow interior pathway of the musical instrument as a mist.

12. The method of claim 7 further comprising adjusting a rate at which the disinfectant agent travels from the source to the musical instrument.

\* \* \* \* \*